US006488935B1

(12) United States Patent
De Villiers Zur Hausen et al.

(10) Patent No.: US 6,488,935 B1
(45) Date of Patent: Dec. 3, 2002

(54) PAPILLOMA VIRUSES, PRODUCTS FOR THE DETECTION THEREOF AS WELL AS FOR TREATING DISEASES CAUSED BY THEM

(75) Inventors: Ethel-Michelle De Villiers Zur Hausen; Harald Zur Hausen, both of Waldmichelbach (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/485,973

(22) PCT Filed: Aug. 12, 1998

(86) PCT No.: PCT/DE98/02379

§ 371 (c)(1),
(2), (4) Date: May 26, 2000

(87) PCT Pub. No.: WO99/09177

PCT Pub. Date: Feb. 25, 1999

(30) Foreign Application Priority Data

Aug. 13, 1997 (DE) .......................................... 197 35 118

(51) Int. Cl.[7] .......................... A61K 39/12; C12N 15/00
(52) U.S. Cl. ............................... 424/204.1; 424/186.1; 424/199.1; 435/69.1; 435/320.1; 435/69.3; 530/300; 530/350; 530/403; 536/23.72
(58) Field of Search .......................... 424/186.1, 204.1, 424/199.1; 435/69.3, 69.1, 252.3, 320.1; 530/350, 300, 403; 536/23.72

(56) References Cited

U.S. PATENT DOCUMENTS 6,025,163 A * 2/2000 Shamanin et al. ......... 435/69.3

FOREIGN PATENT DOCUMENTS

| DE | 197 35 118 C1 | 8/1998 |
|---|---|---|
| EP | 0 235 004 A2 | 9/1987 |
| EP | 0 451 550 A2 | 10/1991 |
| WO | WO 95/30754 A1 | 11/1995 |
| WO | WO 97/04099 A2 | 2/1997 |
| WO | WO 98/23752 A2 | 6/1998 |
| WO | WO 98/42847 A2 | 10/1998 |

OTHER PUBLICATIONS

Astori et al., 1998, "Human Papillomavirus are Commonly Found in Normal Skin of Immunocompetent Hosts," 110:752–755.
Astori et al., 1998, "The papillomaviru found in benign and malignant cutaneous lesions are present in normal skin," *EMBL Sequence Database*. Accession No.: AJ000148, clone DL314.
Berkhout et al., 1995, "Nested PCR approach for detection and typing of epidermodysplasia verruciformis–associated human papillomavirus types in cutaneous cancers from renal transplant recipients," *EMBL Sequence Database*. Accession No.: L38914, clone ICPX1.
Chan et al., 1992, "Phylogenetic Analysis of 48 Papillomavirus Types and 28 Subtypes and Variants: a Showcase for the Molecular Evolution of DNA Viruses," *Journal of Virology* 66(10):5714–5725.
de Villiers et al., 1998, "An interlaboratory study to determine the presence of human papillomavirus DNA in esophageal carcinoma from China," *EMBL Sequence Database*. Accession Nos.: AJ000149, clone DL347 and AJ000150, clone DL369.
Delius and Hofmann, 1994, "Primer–Directed Sequencing of Human Papillomavirus Types," *Current Topics in Microbiology and Immunology* 186:13–31.
Hopfl et al., 1997, "Human papillomavirus DNA in non–melanoma skin cancers of a renal transplant recipient: detection of a new sequence related to epidermodysplasia verruciformis associated types," *EMBL Sequence Database*. Accession No.: U85660, clone RTRX7.
Kirnbauer et al., 1993, "Efficient Self–Assembly of Human Papillomavirus Type 16 L1 and L1–L2 into Virus–Like Particles," *Journal of Virology* 67(12):6929–6936.
Pierceall et al., 1991, "Presence fo Human Papilloma Virus Type 16 DNA Sequences in Human Nonmelanoma Skin Cancers," *J. Invest. Dermatol.* 97:880–884.
Shamanin et al., 1994, "Development of a broad spectrum PCR assay for papillomaviruses and its application in screening lung cancer biopsies," *Journal of General Virology* 75:1149–1156.
Shamanin et al., 1994, "Specific Types of Human Papillomavirus Found in Benign Proliferations and Carcinomas of the Skin in Immunosuppressed Patients," *Cancer Research* 54:4610–4613.
Shamin et al., 1996, "Human Papillomavirus Infections in Nonmelanoma Skin Cancers From Renal Transplant Recipients and Nonimmunosuppressed Patients," *Journal of the National Cancer Institute* 88(12):802–811.
zur Hausen, 1977, "Human Papillomaviruses and Their Possible Role in Squamous Cell Carcinomas," *Curr. Top. Microbiol. Immunol.* 78:1–30.
zur Hausen, 1996, "Papillomavirus infections—a major cause of human cancers," *Biochimica et Biophysica Acta* 1288:F55–F78.

* cited by examiner

*Primary Examiner*—Ali R. Salimi
(74) *Attorney, Agent, or Firm*—Pennie & Edmonds LLP

(57) ABSTRACT

The present invention relates to a DNA coding for a peptide of a papilloma virus major capsid protein and a papilloma virus genome, respectively. Furthermore, the present invention concerns proteins coded by the papilloma virus genome and antibodies directed thereagainst as well as the use thereof for diagnosis, treatment and vaccination.

23 Claims, 7 Drawing Sheets

FIG. 1

DL314.seq  from: 1 to: 380

```
            AATCAGCTGTTTATTACAGTGGCTGATAACACTCGAAACACAAATTTCACTATTAGTGTT
   1        ---------+---------+---------+---------+---------+---------+  60
            TTAGTCGACAAATAATGTCACCGACTATTGTGAGCTTTGTGTTTAAAGTGATAATCACAA

N  Q  L  F  I  T  V  A  D  N  T  R  N  T  N  F  T  I  S  V   -

ACTACAGATGCTGGGGATATAAATGAATATACAGCCACAAATGTTAGAGAATTTTTAAGA
   61       ---------+---------+---------+---------+---------+---------+ 120
            TGATGTCTACGACCCCTATATTTACTTATATGTCGGTGTTTACAATCTCTTAAAAATTCT

T  T  D  A  G  D  I  N  E  Y  T  A  T  N  V  R  E  F  L  R   -

CATGTAGAAGAATTTCAAATATCAATTATTTTACAATTATGTAAGGTTCCTTTAGTTCCA
  121       ---------+---------+---------+---------+---------+---------+ 180
            GTACATCTTCTTAAAGTTTATAGTTAATAAAATGTTAATACATTCCAAGGAAATCAAGGT

H  V  E  E  F  Q  I  S  I  I  L  Q  L  C  K  V  P  L  V  P   -

GAAGTTTTATCACAGATAAATGCTATGAATTCAGGAATATTGGAAGAGTGGCAATTAGGA
  181       ---------+---------+---------+---------+---------+---------+ 240
            CTTCAAAATAGTGTCTATTTACGATACTTAAGTCCTTATAACCTTCTCACCGTTAATCCT

E  V  L  S  Q  I  N  A  M  N  S  G  I  L  E  E  W  Q  L  G   -

TTTGTACCCACGCCAGACAATGCTGTACATGATACATATAGATACATTAACTCAAAAGCA
  241       ---------+---------+---------+---------+---------+---------+ 300
            AAACATGGGTGCGGTCTGTTACGACATGTACTATGTATATCTATGTAATTGAGTTTTCGT

F  V  P  T  P  D  N  A  V  H  D  T  Y  R  Y  I  N  S  K  A   -

ACAAAATGTCCAGATGCTGCAACAGCTGAACAAAAGGAAGATCCTTTTGGTAAATTTACA
  301       ---------+---------+---------+---------+---------+---------+ 360
            TGTTTTACAGGTCTACGACGTTGTCGACTTGTTTTCCTTCTAGGAAAACCATTTAAATGT

T  K  C  P  D  A  A  T  A  E  Q  K  E  D  P  F  G  K  F  T   -

TTTTGGAATGTAGATCTATC
  361       ---------+---------+ 380
            AAAACCTTACATCTAGATAG

MAP of: DL347.seq  from: 1 to: 389

```
    AATCAAATGTTTATTACTGTGGTAGACAACACACGAAACACTAATTTCAGTATTTCAGTC
  1 ---------+---------+---------+---------+---------+---------+ 60
    TTAGTTTACAAATAATGACACCATCTGTTGTGTGCTTTGTGATTAAAGTCATAAAGTCAG

N  Q  M  F  I  T  V  V  D  N  T  R  N  T  N  F  S  I  S  V   -

TATACTGAAGGTGGACAAATAAAAGATATCAGGGACTATACATCTACACAGTTCAGGGAA
 61 ---------+---------+---------+---------+---------+---------+ 120
    ATATGACTTCCACCTGTTTATTTTCTATAGTCCCTGATATGTAGATGTGTCAAGTCCCTT

Y  T  E  G  G  Q  I  K  D  I  R  D  Y  T  S  T  Q  F  R  E   -

TATTTAAGACATGTGGAAGAATATGAAATATCAGTCATATTGCAGTTATGTAAAATACCT
121 ---------+---------+---------+---------+---------+---------+ 180
    ATAAATTCTGTACACCTTCTTATACTTTATAGTCAGTATAACGTCAATACATTTTATGGA

Y  L  R  H  V  E  E  Y  E  I  S  V  I  L  Q  L  C  K  I  P   -

TTGAAGGCTGAAGTTTTAGCCCAGATAAATGCAATGAACTCCTCGTTATTGGAAGACTGG
181 ---------+---------+---------+---------+---------+---------+ 240
    AACTTCCGACTTCAAAATCGGGTCTATTTACGTTACTTGAGGAGCAATAACCTTCTGACC

L  K  A  E  V  L  A  Q  I  N  A  M  N  S  S  L  L  E  D  W   -

CAATTAGGATTTGTGCCTACACCTGATAATCCCATTCATGATACCTACAGATTTATTGAT
241 ---------+---------+---------+---------+---------+---------+ 300
    GTTAATCCTAAACACGGATGTGGACTATTAGGGTAAGTACTATGGATGTCTAAATAACTA

Q  L  G  F  V  P  T  P  D  N  P  I  H  D  T  Y  R  F  I  D   -

TCCTTGGCAACCCGATGCCCTGACAAAAATCCCCCAAAAGAAAAACCTGACCCTTATGAA
301 ---------+---------+---------+---------+---------+---------+ 360
    AGGAACCGTTGGGCTACGGGACTGTTTTTAGGGGGTTTTCTTTTTGGACTGGGAATACTT

S  L  A  T  R  C  P  D  K  N  P  P  K  E  K  P  D  P  Y  E   -

GGCTTAAACTTTTGGAATGTTGATCTAAC
361 ---------+---------+--------- 389
    CCGAATTTGAAAACCTTACAACTAGATTG

DL369.seq from: 1 to: 380

```
        AATCAGATGTTTGTTACTGTAGCAGATAATACAAGAAATACTAATTTTAGTATTAGTGTA
   1    ------------+---------+---------+---------+---------+---------+ 60
        TTAGTCTACAAACAATGACATCGTCTATTATGTTCTTTATGATTAAAATCATAATCACAT

N  Q  M  F  V  T  V  A  D  N  T  R  N  T  N  F  S  I  S  V   -

TCTACAGATGGCAATATACCACAGGAATATGATTCTTCAAATATTAGAGAATTTTTAAGA
  61    ------------+---------+---------+---------+---------+---------+ 120
        AGATGTCTACCGTTATATGGTGTCCTTATACTAAGAAGTTTATAATCTCTTAAAAATTCT

S  T  D  G  N  I  P  Q  E  Y  D  S  S  N  I  R  E  F  L  R   -

CACGTGGAAGAATATCAAATTTCAGTAATTTTGCAGCTATGTAAAGTATCATTGGATCCA
 121    ------------+---------+---------+---------+---------+---------+ 180
        GTGCACCTTCTTATAGTTTAAAGTCATTAAAACGTCGATACATTTCATAGTAACCTAGGT

H  V  E  E  Y  Q  I  S  V  I  L  Q  L  C  K  V  S  L  D  P   -

GATATTTTAGCTCAAATCAATGCTATGAATTCTGGAATCTTAGAAGACTGGCAATTAGGG
 181    ------------+---------+---------+---------+---------+---------+ 240
        CTATAAAATCGAGTTTAGTTACGATACTTAAGACCTTAGAATCTTCTGACCGTTAATCCC

D  I  L  A  Q  I  N  A  M  N  S  G  I  L  E  D  W  Q  L  G   -

TTTATTCCTGTCCCAGATAACTCAGTTCATGACACATACAGATATATTAATTCATTAGCT
 241    ------------+---------+---------+---------+---------+---------+ 300
        AAATAAGGACAGGGTCTATTGAGTCAAGTACTGTGTATGTCTATATAATTAAGTAATCGA

F  I  P  V  P  D  N  S  V  H  D  T  Y  R  Y  I  N  S  L  A   -

ACTAAATGTCCAGCTAAAGTACCACCGACAGAAAGAGAAGATCCTTTTGCTAAGTATGTG
 301    ------------+---------+---------+---------+---------+---------+ 360
        TGATTTACAGGTCGATTTCATGGTGGCTGTCTTTCTCTTCTAGGAAAACGATTCATACAC

T  K  C  P  A  K  V  P  P  T  E  R  E  D  P  F  A  K  Y  V   -

TTCTGGAATGTAGATCTAAC
 361    ------------+-------+ 380
        AAGACCTTACATCTAGATTG

GA1-3 from: 1 to: 437

```
     AATCAACTGTTTATTACAGTGGTGGACAACACAAGAAACACAAACTTCAGTATTAGTGTG
  1  ---------+---------+---------+---------+---------+---------+  60
     TTAGTTGACAAATAATGTCACCACCTGTTGTGTTCTTTGTGTTTGAAGTCATAATCACAC

N  Q  L  F  I  T  V  V  D  N  T  R  N  T  N  F  S  I  S  V   -

TATAGTGAAGCAGGTAAAGTAAAGGATATTTCAGATTATGATGCAAACAAATTTAGGGAA
 61  ---------+---------+---------+---------+---------+---------+ 120
     ATATCACTTCGTCCATTTCATTTCCTATAAAGTCTAATACTACGTTTGTTTAAATCCCTT

Y  S  E  A  G  K  V  K  D  I  S  D  Y  D  A  N  K  F  R  E   -

TATCAAAAACATGTAGAAGAATATGAAATTTCTTTAATATTACAACTATGTAAGATACCT
121  ---------+---------+---------+---------+---------+---------+ 180
     ATAGTTTTTGTACATCTTCTTATACTTTAAAGAAATTATAATGTTGATACATTCTATGGA

Y  Q  K  H  V  E  E  Y  E  I  S  L  I  L  Q  L  C  K  I  P   -

TTAAAAGCCGACGTGTTGGCACAAATTAATGCAATGAATCCATCGTTATTAGAAGAGTGG
181  ---------+---------+---------+---------+---------+---------+ 240
     AATTTTCGGCTGCACAACCGTGTTTAATTACGTTACTTAGGTAGCAATAATCTTCTCACC

L  K  A  D  V  L  A  Q  I  N  A  M  N  P  S  L  L  E  E  W   -

CAAGTGGGGTTTGTACCTGCACCAGACAATCCATTGCAAAGTACCTATAGGTATATCGAT
241  ---------+---------+---------+---------+---------+---------+ 300
     GTTCACCCCAAACATGGACGTGGTCTGTTAGGTAACGTTTCATGGATATCCATATAGCTA

Q  L  G  F  V  P  A  P  D  N  P  L  Q  S  T  Y  R  Y  I  D   -

AGCTTGGCCACACCATGTCCTGATAAAGTGCCTACCAAAGAAAAGGAAGATCCATATGCT
301  ---------+---------+---------+---------+---------+---------+ 360
     TCGAACCGGTGTGGTACAGGACTATTTCACGGATGGTTTCTTTTCCTTCTAGGTATACGA

S  L  A  T  P  C  P  D  K  V  P  T  K  E  K  E  D  P  Y  A   -

CCGTTTACATTTTGGAACGTTGATTTGACAGAAAGACTTTCCTTGGAACTGGATCAATAT
361  ---------+---------+---------+---------+---------+---------+ 420
     GGCAAATGTAAAACCTTGCAACTAAACTGTCTTTCTGAAAGGAACCTTGACCTAGTTATA

P  F  T  F  W  N  V  D  L  T  E  R  L  S  L  E  L  D  Q  Y   -

TCTCTGGGACGAAAGTT
421  ---------+------- 437
     AGAGACCCTGCTTTCAA

GA3-1 from: 1 to: 437

```
    AATCAGATGTTTATTACTGTTGTAGACAACACACGCAGCACAAATTTTAGTATATCAGTT
  1 ---------+---------+---------+---------+---------+---------+ 60
    TTAGTCTACAAATAATGACAACATCTGTTGTGTGCGTCGTGTTTAAAATCATATAGTCAA

N  Q  M  F  I  T  V  V  D  N  T  R  S  T  N  F  S  I  S  V   -

CACACAGAAAATCAAGATATATCTAAAATTGACAGTTTTGATGCAACTCAGTTTAGGGAA
 61 ---------+---------+---------+---------+---------+---------+ 120
    GTGTGTCTTTTAGTTCTATATAGATTTTAACTGTCAAAACTACGTTGAGTCAAATCCCTT

H  T  E  N  Q  D  I  S  K  I  D  S  F  D  A  T  Q  F  R  E   -

TACTTAAGACATGTAGAGGAATATGAGATTTCTATAATATTACAGTTATGTAAGATTCCT
121 ---------+---------+---------+---------+---------+---------+ 180
    ATGAATTCTGTACATCTCCTTATACTCTAAAGATATTATAATGTCAATACATTCTAAGGA

Y  L  R  H  V  E  E  Y  E  I  S  I  I  L  Q  L  C  K  I  P   -

CTGAAAGCAGAAGTCTTAGCACAAATTAATGCAATGAATTCTTCATTACTTGAAGACTGG
181 ---------+---------+---------+---------+---------+---------+ 240
    GACTTTCGTCTTCAGAATCGTGTTTAATTACGTTACTTAAGAAGTAATGAACTTCTGACC

L  K  A  E  V  L  A  Q  I  N  A  M  N  S  S  L  L  E  D  W   -

CAACTTGGCTTTGTGCCGACGCCTGATAATCCAATTCATGATACGTACAGATATATTGAT
241 ---------+---------+---------+---------+---------+---------+ 300
    GTTGAACCGAAACACGGCTGCGGACTATTAGGTTAAGTACTATGCATGTCTATATAACTA

Q  L  G  F  V  P  T  P  D  N  P  I  H  D  T  Y  R  Y  I  D   -

TCTTTGGCAACACGGTGCCCTGATAAGACGCCTCCAAAGGAAAAACCTGATCCATATGAA
301 ---------+---------+---------+---------+---------+---------+ 360
    AGAAACCGTTGTGCCACGGGACTATTCTGCGGAGGTTTCCTTTTTGGACTAGGTATACTT

S  L  A  T  R  C  P  D  K  T  P  P  K  E  K  P  D  P  Y  E   -

AAGTTACATTTTTGGAATGTGGACCTTACCGAACGTCTGTCTTTAGATTTAGATCAATAT
361 ---------+---------+---------+---------+---------+---------+ 420
    TTCAATGTAAAAACCTTACACCTGGAATGGCTTGCAGACAGAAATCTAAATCTAGTTATA

K  L  H  F  W  N  V  D  L  T  E  R  L  S  L  D  L  D  Q  Y   -

CCTCTGGGACGAAAGTT
421 ---------+------- 437
    GGAGACCCTGCTTTCAA

GA6-2 from: 1 to: 389

```
     AATCAAATGTTTATTACAGTTGTAGACAACACGCGAAACACCAATTTCAGTATATCTATA
  1  ---------+---------+---------+---------+---------+---------+  60
     TTAGTTTACAAATAATGTCAACATCTGTTGTGCGCTTTGTGGTTAAAGTCATATAGATAT

N  Q  M  F  I  T  V  V  D  N  T  R  N  T  N  F  S  I  S  I  -

TCTAGTGAAAATCAAGATATACAGCAAATACAATCATATGACTCACAAAAGTTTAGGGAA
 61  ---------+---------+---------+---------+---------+---------+ 120
     AGATCACTTTTAGTTCTATATGTCGTTTATGTTAGTATACTGAGTGTTTTCAAATCCCTT

S  S  E  N  Q  D  I  Q  Q  I  Q  S  Y  D  S  Q  K  F  R  E  -

TATTTAAGGCACGTAGAAGAATATGAAATTTCTATTATTTTACAGTTGTGTAAGATTCCA
121  ---------+---------+---------+---------+---------+---------+ 180
     ATAAATTCCGTGCATCTTCTTATACTTTAAAGATAATAAAATGTCAACACATTCTAAGGT

Y  L  R  H  V  E  E  Y  E  I  S  I  I  L  Q  L  C  K  I  P  -

CTACAAGCAGAAGTTTTAGCACAAATAAATGCAATGAACCCCTCCTTACTAGAGGATTGG
181  ---------+---------+---------+---------+---------+---------+ 240
     GATGTTCGTCTTCAAAATCGTGTTTATTTACGTTACTTGGGGAGGAATGATCTCCTAACC

L  Q  A  E  V  L  A  Q  I  N  A  M  N  P  S  L  L  E  D  W  -

CAGTTAGGATTTGTGCCAACTCCCGATAATCCTATCCAGGACACATACAGATTTATTGAT
241  ---------+---------+---------+---------+---------+---------+ 300
     GTCAATCCTAAACACGGTTGAGGGCTATTAGGATAGGTCCTGTGTATGTCTAAATAACTA

Q  L  G  F  V  P  T  P  D  N  P  I  Q  D  T  Y  R  F  I  D  -

TCCTTAGCTACCAGGTGTCCCGATAAAAATCCACCAAAGGAAAAACCTGATCCTTATGAA
301  ---------+---------+---------+---------+---------+---------+ 360
     AGGAATCGATGGTCCACAGGGCTATTTTTAGGTGGTTTCCTTTTTGGACTAGGAATACTT

S  L  A  T  R  C  P  D  K  N  P  P  K  E  K  P  D  P  Y  E  -

AAATTAACATTCTGGAATGTAGATCTAAC
361  ---------+---------+--------- 389
     TTTAATTGTAAGACCTTACATCTAGATTG

GA9-4 from: 1 to: 380

```
    AATCAACTGTTTGTTACAGTTGCAGATAATACAAGGAATACCAATTTTACTATAAGTGTA
  1 ---------+---------+---------+---------+---------+---------+ 60
    TTAGTTGACAAACAATGTCAACGTCTATTATGTTCCTTATGGTTAAAATGATATTCACAT

N  Q  L  F  V  T  V  A  D  N  T  R  N  T  N  F  T  I  S  V  -

ACATCTAATGGTACCCCCATAGCAGAATATGATTCCAAAACTATTAGAGAATTTTTAAGG
 61 ---------+---------+---------+---------+---------+---------+ 120
    TGTAGATTACCATGGGGGTATCGTCTTATACTAAGGTTTTGATAATCTCTTAAAAATTCC

T  S  N  G  T  P  I  A  E  Y  D  S  K  T  I  R  E  F  L  R  -

CACGTAGAAGAATATCAGTTGTCCATGATATTGCAATTATGTAAAGTACCTTTAAAAGCA
121 ---------+---------+---------+---------+---------+---------+ 180
    GTGCATCTTCTTATAGTCAACAGGTACTATAACGTTAATACATTTCATGGAAATTTTCGT

H  V  E  E  Y  Q  L  S  M  I  L  Q  L  C  K  V  P  L  K  A  -

GAAGTTTTATCCCAGATTAATGCTATGAATTCAGGTATTTTGGAGGAGTGGCAGTTAGGT
181 ---------+---------+---------+---------+---------+---------+ 240
    CTTCAAAATAGGGTCTAATTACGATACTTAAGTCCATAAAACCTCCTCACCGTCAATCCA

E  V  L  S  Q  I  N  A  M  N  S  G  I  L  E  E  W  Q  L  G  -

TTTGTGCCTACACCAGACAACTCTGTACATGATATTTATAGATATATTGACTCAAAAGCA
241 ---------+---------+---------+---------+---------+---------+ 300
    AAACACGGATGTGGTCTGTTGAGACATGTACTATAAATATCTATATAACTGAGTTTTCGT

F  V  P  T  P  D  N  S  V  H  D  I  Y  R  Y  I  D  S  K  A  -

ACAAAATGTCCCGATGCAGTGCCTGCAAAAGAAAAAGAAGATCCATTTGACAAATATACA
301 ---------+---------+---------+---------+---------+---------+ 360
    TGTTTTACAGGGCTACGTCACGGACGTTTTCTTTTTCTTCTAGGTAAACTGTTTATATGT

T  K  C  P  D  A  V  P  A  K  E  K  E  D  P  F  D  K  Y  T  -

TTTTGGAATGTAGATCTAAC
361 ---------+---------+ 380
    AAAACCTTACATCTAGATTG

F  W  N  V  D  L  -
```

US 6,488,935 B1

PAPILLOMA VIRUSES, PRODUCTS FOR THE DETECTION THEREOF AS WELL AS FOR TREATING DISEASES CAUSED BY THEM

This is a national phase filing of the Application No. PCT/DE98/02379, which was filed with the Patent Corporation Treaty on Aug. 12, 1998, and is entitled to priority of the German Patent Application 197 35 118.2, filed Aug. 13, 1997.

I. FIELD OF THE INVENTION

This invention relates to a DNA coding for a peptide of a papilloma virus major capsid protein and a papilloma virus genome, respectively. In addition, this invention concerns proteins coded by the papilloma virus genome and antibodies directed against them as well as their use for diagnosis, treatment and vaccination.

II. BACKGROUND OF THE INVENTION

It is known that papilloma viruses infect the epithelium of human beings and animals. Human papilloma viruses (hereinafter referred to as HP viruses) are found in benign epithelial neoplasms, e.g., warts, condylomas in the genital zone, and malignant epithelial neoplasms, e.g., carcinomas of the skin and the uterus. Zur Hausen, H., 1996, *Biochimica et Biophysica Acta* (BBA) 1288:55–78). HP Viruses are also considered for the growth of malignant tumors in the oropharyngeal zone. Zur Hausen, H., 1977, *Curr. Top. Microbiol. Immunol.* 78:1–30).

Papilloma viruses have an icosahedral capsid without envelope in which a circular, double-stranded DNA molecule of about 7900 bp is present. The capsid comprises a major capsid protein (11) and a minor capsid protein (L2). Both proteins, coexpressed or L1 expressed alone, result in vitro in the formation of virus-like particles. Kirnbauer et al., 1993, *Journal of Virology* 67:6929–6936.

Papilloma viruses cannot be proliferated in monolayer cell culture. Therefore, their characterization is extremely difficult, the detection of papilloma viruses already creating considerable problems. This applies especially to papilloma viruses in carcinomas of the skin.

Thus, it is the object of the present invention to provide a product by which papilloma viruses can be detected, particularly in carcinomas of the skin. Furthermore, a product should be provided to be able to take therapeutic steps against these papilloma viruses.

III. SUMMARY OF THE INVENTION

The present invention relates to a DNA coding for a peptide of a papilloma virus major capsid protein and a papilloma virus genome, respectively. Furthermnore, the present invention concerns proteins coded by the papilloma virus genome and antibodies directed thereagainst as well as the use thereof for diagnosis, treatment and vaccination.

IV. BRIEF DESCRIPTION OF THE DRAWINGS

FIG. 1 shows the base sequence and the amino acid sequence, derived therefrom, of a DNA coding for a peptide of L1 of a papilloma virus. This DNA was deposited as plasmid DL314 with DSMZ (Deutsche Sammlung von Microorganismen und Zellkulturen [German-type collection of micro-organisms and cell cultures]) under DSM 11604 on Jun. 12, 1997.

FIG. 2 shows the base sequence and the amino acid sequence, derived therefrom, of a DNA coding for a peptide of L1 of a papilloma virus. This DNA was deposited as plasmid DL347 with DSMZ under DMS 11605 on Jun. 12, 1997.

FIG. 3 shows the base sequence and the amino acid sequence, derived therefrom, of a DNA coding for a peptide of L1 of a papilloma virus. This DNA was deposited as plasmid DL369 with DSMZ under DSM 11606 on Jun. 12, 1997.

FIG. 4 shows the base sequence and the amino acid sequence, derived therefrom, of a DNA coding for a peptide of L1 of a papilloma virus. This DNA was deposited as plasmid GA1-3 with DSMZ under DSM 11607 on Jun. 12, 1997.

FIG. 5 shows the base sequence and the amino acid sequence, derived therefrom, of a DNA coding for a peptide of L1 of a papilloma virus. This DNA was deposited as plasmid GA3-1 with DSMZ under DSM 11608 on Jun. 12, 1997.

FIG. 6 shows the base sequence and the amino acid sequence, derived therefrom, of a DNA coding for a peptide of L1 of a papilloma virus. This DNA was deposited as plasmid GA6-2 with DSMZ under DSM 11609 on Jun. 12, 1997.

FIG. 7 shows the base sequence and the amino acid sequence, derived therefrom, of a DNA coding for a peptide of L1 of a papilloma virus. This DNA was deposited as plasmid GA9-4 with DSMZ under DSM 11610 on Jun. 12, 1997.

V. DETAILED DESCRIPTION OF THE INVENTION

It is the object of the present invention to provide a product by which papilloma viruses can be detected, particularly in carcinomas of the skin. Furthermore, a product should be provided to be able to take therapeutic steps against these papilloma viruses. According to the invention this is achieved by providing the subject matters in the claims.

Therefore, the subject matter of the invention relates to a DNA coding for a peptide of a papilloma virus major capsid protein (L1), the peptide comprising the amino acid sequence of FIG. 1, FIG. 2, FIG. 3, FIG. 4, FIG. 5, FIG. 6, or FIG. 7, or an amino acid sequence differing therefrom by one or more amino acids.

A further subject matter of the invention relates to a DNA coding for a peptide of a papilloma virus major capsid protein, the DNA comprising the base sequence of FIG. 1, FIG. 2, FIG. 3, FIG. 4, FIG. 5, FIG. 6, or FIG. 7 or a base sequence differing therefrom by one or more base pairs.

The above DNA was compared with the DNA of known papilloma viruses. Sequence homology studies were carried out. A homology having less than 90% shows that a DNA according to the invention is a new HP virus. The DNAs according to the invention have the following sequence homologies with respect to known papilloma viruses:

DNA of FIG. 1: 78% with respect to HP virus 15
DNA of FIG. 2: 80% with respect to HP virus 5b
DNA of FIG. 3: 76% with respect to HP virus 15
DNA of FIG. 4: 80% with respect to HP virus 24
DNA of FIG. 5: 79% with respect to HP virus 8
DNA of FIG. 6: 81% with respect to HP virus 12
DNA of FIG. 7: 84% with respect to HP virus 15.

According to the invention, the above DNA can be present in a vector and expression vector, respectively. A person skilled in the art is familiar with examples thereof. In the case of an expression vector for *E. coli* these are, e.g., pGEMEX, pUC derivatives, pGEM-T and pGEX-2T. For the expression in yeast, e.g., pY100 and Ycpad1 have to be mentioned, while for the expression in animal cells, e.g., pKCR, pEF-BOS, cDM8 and pCEV4 have to be indicated.

The person skilled in the art knows suitable cells to express the above DNA present in an expression vector. Examples of such cells comprise the *E. coli* strains HP101, DH1, x1776, JM101, JM 109, and XL1-Blue, the yeast strain Saccharomyces cerevisiae and the animal cells L, NH-3T3, FM3A, CHO, COS, Vero, and HeLa.

The person skilled in the art knows in which way the above DNA has to be inserted in an expression vector. He is also familiar with the fact that the above DNA can be inserted in connection with a DNA coding for another protein and peptide, respectively, so that the above DNA can be expressed in the form of a fusion protein.

A further subject matter of the invention relates to a papilloma virus genome which comprises the above DNA. The expression "papilloma virus genome" also comprises an incomplete genome, i.e., fragments of a papilloma virus genome, which comprise the above DNA. This may be, e.g., a DNA coding for L1 or a portion thereof.

A common process can be used for the provision of the above papilloma virus genome. It is favorable to use a process which comprises the following processing steps:

(a) isolation of the total DNA from a biopsy of epithelial neoplasm, (b) hybridization of the total DNA of (a) with the above DNA so as to detect a papilloma virus genome included in the total DNA of (a), and (c) cloning of the total DNA of (a) containing the papilloma virus geome, in a vector and optionally subcloning the result clone, all processing steps originating from common DNA recombination technique.

As far as the isolation, hybridization and cloning of cell DNA is concerned, reference is made by way of supplement to Sambrook et al., *Molecular Cloning, A Laboratory Manual*, second edition, Cold Spring Harbor Laboratory (1989).

The expression "epithelial neoplasm" comprises any neoplasms of epithelium in man and animal. Examples of such neoplasms are warts, condylomas in the genital zone and carcinomas of the skin. The latter are used preferably to isolate the above papilloma virus genome.

The expression "vector" comprises any vectors suitable for cloning chromosomal DNA and extrachromosomal DNA, respectively. Examples of such vectors are cosmids such as pWE15 and Super Cos1, and phages such as λ-phages, e.g., λZAP expression vector, λZAPII vector and λgt10 vector. In the present case, λ-phages are used preferably. The above vectors are known and obtainable from the company of Stratagene.

Papilloma virus genomes according to the invention may be present in integrated form in chromosomal DNA or in extrachromosomal fashion. The person skilled in the art is familiar with processes serving the clarification thereof. He also knows processes serving for finding out the optimum restriction enzymes for cloning the papilloma virus genomes. He will orient himself by genomes of known papilloma viruses. In particular, the person skilled in the art will pay corresponding attention to the above-mentioned HP viruses.

The provision of a papilloma virus genome referred to as DL314-G is described by way of example. For this purpose, the total DNA is isolated from a biopsy of a basal cell carcinoma, cleaved by BamHI and separated electrophoretically in an agarose gel. The agarose gel is then subjected to a blotting method so as to transfer the DNA to a nitrocellulose membrane. It is inserted in a hybridization method in which the DNA of FIG. 1 is used as labeled sample, optionally in combination with a DNA of HP virus 15. Hybridization with the papilloma virus DNA present in the total DNA is obtained.

Moreover, the above total DNA cleaved by BamHI is cloned in a λ-phage. The corresponding clones, i.e., the clones containing the papilloma virus DNA are identified by hybridization with the DNA of FIG. 1, optionally in combination with DNA of the HP virus 15. The insert of these clones is then subjected to a further cloning in a plasmid vector so as to obtain a clone which contains the papilloma virus genome DL314-G. The genome is confirmed by sequencing.

Further papilloma virus genomes are provided analogously. They are designated in accordance with the DNAs used for their provision, namely by: DL347-G, DL369-G, GA1-3-G, GA3-1-G, GA6-2-G, and GA9-4-G, respectively.

A further subject matter of the invention relates to a protein which is coded by the above papilloma virus genome. Such a protein is, e.g., a major capsid protein (L1) or a minor capsid protein (L2). An above protein is prepared as usual. The preparation of L1 and L2, respectively, of the papilloma virus genome DL314-G is described by way of example. For this purpose, the HP virus 15 related to the DNA of FIG. 1 is used. The full sequence and the position of individual DNA regions coding for proteins are known in connection therewith. These DNAS are identified on the papilloma virus genome DL314-G by parallel restriction cleavages of both genomes and subsequent hybridization with various fragments concerning the DNA encoding L1 and L2, respectively. They are confirmed by sequencing. The DNA coding for L1 is referred to as DL314-G-L1 DNA and the DNA coding for L2 is referred to as DL314-G-L2 DNA.

Furthermore, the DNA coding for L1 and L2, respectively, is inserted in an expression vector Examples thereof are mentioned above for *E. coli*, yeast and animal cells. In particular, reference is made to the vector pGEX-2T as regards the expression in *E. coli*. Kirnbauer, et al., supra). Having inserted the DL314-G-L1 DNA and DL314-G-L2 DNA, one obtains pGEX-2T-DL314-G-L1 and pGEX-2T-DL314-G-L2, respectively. After transforming *E. coli*, these expression vectors express a glutathion S transferase L1 fusion protein and glutathione S transferase 12 fusion protein, respectively. The proteins are purified as usual.

The bacculovirus system and vaccinia virus system, respectively, is mentioned for a further expression of the above DNA encoding L1 and L2, respectively. Expression vectors usable for this purpose are, e.g., pEV mod. and pSynwtVI⁻ for the bacculovirus system (Kirnbauer et al., supra). Especially vectors with the vaccinia virus "early" (p7.5k) promoter and "late" (Psynth, p11K) promoter, respectively, have to be mentioned for the vaccinia virus system. Hagensee et al., 1993, *Journal of Virology* 67:315–3220. The bacculovirus system is preferred in the present case. Having inserted the above DNA encoding L1 and L2, respectively, in pEV mod., one obtains pEVmod. - DL314-G-L1 and pEVmod.-DL324-G-L2, respectively.

The former expression vector as such or both expression vectors jointly lead to the formation of virus-like particles after infection of SF-9 insect cells. In the former case, such a particle comprises an L1 protein, while in the latter case it contains an L2 protein in addition to an L1 protein.

A virus-like particle of the latter case is also obtained by inserting the above DL314-G-L1 and DL314-G-L2 DNAs jointly in the expression vector pSynwtVi⁻and using the resulting pSynwtVI⁻DL314-G-L1/L2 for the infection of SF-9 insect cells. The above virus-like particles are purified as usual. They also represent a subject matter of the invention.

A further subject matter of the invention relates to an antibody directed against an above protein and virus-like particle, respectively. The preparation thereof is made as usual. It is described by way of example for the preparation of an antibody which is directed against a virus-like particle comprising L1 of DL314-G. For this purpose, the virus-like particle is injected subcutaneously into BALB/c mice. This injection is repeated at intervals of 3 weeks each. About 2 weeks after the last injection, the serum containing the antibody is isolated and tested as usual.

In a preferred embodiment, the antibody is a monoclonal antibody. For its preparation, spleen cells are removed from the mice after the above fourth injection and fused with myeloma cells as usual. The further cloning also takes place according to known methods.

By means of the present invention it is possible to detect papilloma viruses, particularly in carcinomas of the skin. For this purpose, the DNA according to the invention an be used as such or when comprised by a further DNA. The latter may also be a papilloma virus genome or a portion thereof.

The present invention also enables the provision of formerly unknown papilloma viruses. They are found especially in carcinomas of the skin. In addition, the invention supplies proteins and virus-like particles which originate from these papilloma viruses. Moreover, antibodies are provided which are directed against these proteins and particles, respectively.

The present invention also enables to take diagnostic and therapeutic steps in the case of papilloma virus diseases. Moreover, it supplies the possibility of building up a vaccine against papilloma virus infections. Thus, the present invention represents a break-through in the field of papilloma virus research.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Identification of the Papilloma Virus Genome D1314-g

The total DNA is isolated from a biopsy of a basal cell carcinoma. 10 µg of this DNA are cleaved by the restriction enzyme BamHI and separated electrophoretically in a 0.5% agarose gel. At the same time, 10 µg of the above DNA which was not cleaved, is also separated. The agarose gel is subjected to a blotting method so as transfer the DNA from the agarose gel to a nitrocellulose membrane. It is employed in a hybridization method in which the above DNA of FIG. 1 is used in combination with the HP virus-15 DNA as $p^{32}$-labeled sample. Hybridization with the blotted DNA is obtained.

The person skilled in the field of DNA recombination technique is familiar with the above methods. Reference is made to Sambrook et al., supra, by way of supplement.

B. Example 2

Cloning of the Papilloma Virus Genome D1314-g

The biopsy DNA obtained from Example 1 is cleaved by the restriction enzyme BamHi. The resulting fragments are used in a ligase reaction in which the dephosphorylated vector λZAP express cleaved by BamHI is also present. The resulting recombinant DNA molecules are packed in bacteriophages, and they are used or infecting bacteria. For these processing steps, the ZAP express vector kit offered by the company of Stratagene is used. The resulting phage plaques are then subjected to a hybridization process which uses the $p^{32}$-labeled DNA of FIG. 1 employed in Example 1 in combination with $p^{32}$-labeled HP virus-15 DNA. Hybridization with corresponding phage plaques is obtained. The BamHI fragments of DL314-G are isolated therefrom and used in a further ligase reaction together with BamHI-cleaved, dephosphorylated plasmid vector, pBluescript. The resulting recombinant DNA molecules are used for transforming bacteria, *E. coli* XL1-Blue. By restriction cleavages and hybridization with the above DNA samples, respectively, a bacterial clone containing the papilloma virus genome DL314-G is identified. The plasmid of this bacterial clone is referred to as pBlue-DL314-G.

All references cited within the body of the instant specification are hereby incorporated by reference in their entirety.

What is claimed is:

1. An isolated polynucleotide consisting essentially of:
   (a) a nucleotide sequence encoding the peptide of SEQ ID NO:2, SEQ ID NO:4, or SEQ ID NO:6;
   (b) a nucleotide sequence hybridizing to the nucleotide sequence of SEQ ID NO:1, SEQ ID NO:3, or SEQ ID NO:5; or
   (c) the complement of (a) or (b);
   wherein the polynucleotide has a homology of at least 90% to the nucleotide sequence of SEQ ID NO:1, SEQ ID NO:3, or SEQ ID NO:5, or the complement thereof.

2. An isolated polynucleotide encoding a peptide of a papilloma virus major capsid protein, wherein the said polynucleotide has been obtained using the following steps:
   (a) incubating total DNA isolated from a biopsy of epithelial neoplasm with a nucleic acid having at least a portion of the nucleotide sequence of SEQ ID NO:1, SEQ ID NO:3, or SEQ ID NO:5 under a condition that allows hybridization of a polynucleotide derived from a papilloma virus genome included in the total DNA to said nucleotide sequence of the complement of SEQ ID NO:1, SEQ ID NO:3, or SEQ ID NO:5; and
   (b) identifying and isolating a polynucleotide that hybridizes to the complement of the nucleotide sequence of SEQ ID NO:1, SEQ ID NO:3, or SEQ ID NO:5 in step (a);
   wherein the polynucleotide has a homology of at least 90% to the nucleotide sequence of SEQ ID NO:1, SEQ ID NO:3, or SEQ ID NO:5.

3. An isolated polynucleotide, consisting essentially of (a) a nucleic acid encoding a peptide comprising the amino acid sequence of SEQ ID NO:2, SEQ ID NO:4, or SEQ ID NO:6, or (b) the complement of (a).

4. An isolated polynucleotide, wherein the polynucleotide consists essentially of the nucleotide sequence of SEQ ID NO:1, SEQ ID NO:3, or SEQ ID NO:5, or the complement thereof.

5. A plasmid comprising the polynucleotide of claim 1 or 2.

6. A plasmid comprising the polynucleotide of claim 3 or 4.

7. An expression vector comprising the polynucleotide of claim 1 or 2.

8. An expression vector comprising the polynucleotide of claim 3 or 4.

9. A host cell comprising the plasmid of claim 5.

10. A host cell comprising the plasmid of claim 6.

11. A host cell comprising the expression vector of claim 7.

12. A host cell comprising the expression vector of claim 8.

13. A method of producing a peptide of a papilloma virus major capsid protein, comprising cultivating the host cell of claim 11 under suitable conditions.

14. A method of producing a peptide of a papilloma virus major capsid protein, comprising cultivating the host cell of claim 12 under suitable conditions.

15. A method of detecting a papilloma virus DNA, comprising:
    (a) hybridizing under stringent conditions at least a portion of the polynucleotide of claim 1, 2, 3, or 4 to a DNA sample; and
    (b) identifying papilloma virus in said DNA sample by detecting a hybridization signal.

16. A composition comprising the polynucleotide of claim 1, 2, 3, or 4 as reagent for diagnosis and a pharmaceutically acceptable carrier.

17. A method of producing a papilloma virus genome, comprising:
    (a) incubating total DNA isolated from a biopsy of epithlial neoplasm with a nucleic acid having at least a portion of the nucleotide sequence of SEQ ID. NO:1, SEQ ID NO:3, or SEQ ID NO:5, under a condition that allows hybridization of a polynucleotide derived from a papilloma virus genome included in the total DNA to said nucleotide sequence of the complement of SEQ ID NO:1, SEQ ID NO:3, or SEQ ID NO:5; and
    (b) identifying and isolating a polynucleotide that hybridizes to the nucleotide sequence of the complement of SEQ ID NO:1, SEQ ID NO:3, or SEQ ID NO:5 in step (a).

18. The method of claim 17, wherein the polynucleotide has a homology of at least 90% to the nucleotide sequence of SEQ ID NO:1, SEQ ID NO:3, or SEQ ID NO:5.

19. A composition comprising the polynucleotide of claim 1, 2, 3, or 4 as reagent for vaccination and a pharmaceutically acceptable carrier.

20. A method of vaccinating a subject in need against papilloma virus, comprising administering to said subject the composition of claim 19.

21. A method of diagnosing a condition caused by papilloma virus in a subject in need, comprising exposing said subject to the composition of claim 16.

22. A method of using the polynucleotide of claims 1, 2, 5, or 6 as reagent for diagnosis.

23. The method according to claim 22, wherein the diagnosis concerns papilloma virus infections or diseases.

* * * * *

SEQUENCE LISTING

<160> NUMBER OF SEQ ID NOS: 14

<210> SEQ ID NO 1
<211> LENGTH: 380
<212> TYPE: DNA
<213> ORGANISM: Papillomavirus Capsid Protein
<220> FEATURE:
<221> NAME/KEY: CDS
<222> LOCATION: (1)..(378)

<400> SEQUENCE: 1

```
aat cag ctg ttt att aca gtg gct gat aac act cga aac aca aat ttc      48
Asn Gln Leu Phe Ile Thr Val Ala Asp Asn Thr Arg Asn Thr Asn Phe
```

```
                    1                 5                    10                    15
          act att agt gtt act aca gat gct ggg gat ata aat gaa tat aca gcc            96
          Thr Ile Ser Val Thr Thr Asp Ala Gly Asp Ile Asn Glu Tyr Thr Ala
                              20                  25                  30 aca aat gtt aga gaa ttt tta aga cat gta gaa gaa ttt caa ata tca           144
          Thr Asn Val Arg Glu Phe Leu Arg His Val Glu Glu Phe Gln Ile Ser
                      35                  40                  45 att att tta caa tta tgt aag gtt cct tta gtt cca gaa gtt tta tca           192
          Ile Ile Leu Gln Leu Cys Lys Val Pro Leu Val Pro Glu Val Leu Ser
                  50                  55                  60 cag ata aat gct atg aat tca gga ata ttg gaa gag tgg caa tta gga           240
          Gln Ile Asn Ala Met Asn Ser Gly Ile Leu Glu Glu Trp Gln Leu Gly
          65                  70                  75                  80 ttt gta ccc acg cca gac aat gct gta cat gat aca tat aga tac att           288
          Phe Val Pro Thr Pro Asp Asn Ala Val His Asp Thr Tyr Arg Tyr Ile
                              85                  90                  95 aac tca aaa gca aca aaa tgt cca gat gct gca aca gct gaa caa aag           336
          Asn Ser Lys Ala Thr Lys Cys Pro Asp Ala Ala Thr Ala Glu Gln Lys
                      100                 105                 110 gaa gat cct ttt ggt aaa ttt aca ttt tgg aat gta gat cta tc                380
          Glu Asp Pro Phe Gly Lys Phe Thr Phe Trp Asn Val Asp Leu
                  115                 120                 125

<210> SEQ ID NO 2
<211> LENGTH: 126
<212> TYPE: PRT
<213> ORGANISM: Papillomavirus Capsid Protein

<400> SEQUENCE: 2

Asn Gln Leu Phe Ile Thr Val Ala Asp Asn Thr Arg Asn Thr Asn Phe
1               5                   10                  15

Thr Ile Ser Val Thr Thr Asp Ala Gly Asp Ile Asn Glu Tyr Thr Ala
            20                  25                  30

Thr Asn Val Arg Glu Phe Leu Arg His Val Glu Glu Phe Gln Ile Ser
        35                  40                  45

Ile Ile Leu Gln Leu Cys Lys Val Pro Leu Val Pro Glu Val Leu Ser
    50                  55                  60

Gln Ile Asn Ala Met Asn Ser Gly Ile Leu Glu Glu Trp Gln Leu Gly
65                  70                  75                  80

Phe Val Pro Thr Pro Asp Asn Ala Val His Asp Thr Tyr Arg Tyr Ile
                85                  90                  95

Asn Ser Lys Ala Thr Lys Cys Pro Asp Ala Ala Thr Ala Glu Gln Lys
            100                 105                 110

Glu Asp Pro Phe Gly Lys Phe Thr Phe Trp Asn Val Asp Leu
        115                 120                 125

<210> SEQ ID NO 3
<211> LENGTH: 389
<212> TYPE: DNA
<213> ORGANISM: Papillomavirus Capsid Protein
<220> FEATURE:
<221> NAME/KEY: CDS
<222> LOCATION: (1)..(387)

<400> SEQUENCE: 3 aat caa atg ttt att act gtg gta gac aac aca cga aac act aat ttc            48
          Asn Gln Met Phe Ile Thr Val Val Asp Asn Thr Arg Asn Thr Asn Phe
          1               5                   10                  15 agt att tca gtc tat act gaa ggt gga caa ata aaa gat atc agg gac            96
          Ser Ile Ser Val Tyr Thr Glu Gly Gly Gln Ile Lys Asp Ile Arg Asp
```

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |
| tat | aca | tct | aca | cag | ttc | agg | gaa | tat | tta | aga | cat | gtg | gaa | gaa | tat | 144 |
| Tyr | Thr | Ser | Thr | Gln | Phe | Arg | Glu | Tyr | Leu | Arg | His | Val | Glu | Glu | Tyr |  |
|  |  | 35 |  |  |  |  | 40 |  |  |  |  | 45 |  |  |  |  |
| gaa | ata | tca | gtc | ata | ttg | cag | tta | tgt | aaa | ata | cct | ttg | aag | gct | gaa | 192 |
| Glu | Ile | Ser | Val | Ile | Leu | Gln | Leu | Cys | Lys | Ile | Pro | Leu | Lys | Ala | Glu |  |
|  | 50 |  |  |  |  | 55 |  |  |  |  | 60 |  |  |  |  |  |
| gtt | tta | gcc | cag | ata | aat | gca | atg | aac | tcc | tcg | tta | ttg | gaa | gac | tgg | 240 |
| Val | Leu | Ala | Gln | Ile | Asn | Ala | Met | Asn | Ser | Ser | Leu | Leu | Glu | Asp | Trp |  |
| 65 |  |  |  |  | 70 |  |  |  |  | 75 |  |  |  |  | 80 |  |
| caa | tta | gga | ttt | gtg | cct | aca | cct | gat | aat | ccc | att | cat | gat | acc | tac | 288 |
| Gln | Leu | Gly | Phe | Val | Pro | Thr | Pro | Asp | Asn | Pro | Ile | His | Asp | Thr | Tyr |  |
|  |  |  |  | 85 |  |  |  |  | 90 |  |  |  |  | 95 |  |  |
| aga | ttt | att | gat | tcc | ttg | gca | acc | cga | tgc | cct | gac | aaa | aat | ccc | cca | 336 |
| Arg | Phe | Ile | Asp | Ser | Leu | Ala | Thr | Arg | Cys | Pro | Asp | Lys | Asn | Pro | Pro |  |
|  |  |  | 100 |  |  |  |  | 105 |  |  |  |  | 110 |  |  |  |
| aaa | gaa | aaa | cct | gac | cct | tat | gaa | ggc | tta | aac | ttt | tgg | aat | gtt | gat | 384 |
| Lys | Glu | Lys | Pro | Asp | Pro | Tyr | Glu | Gly | Leu | Asn | Phe | Trp | Asn | Val | Asp |  |
|  |  | 115 |  |  |  |  | 120 |  |  |  |  | 125 |  |  |  |  |
| cta | ac |  |  |  |  |  |  |  |  |  |  |  |  |  |  | 389 |
| Leu |  |  |  |  |  |  |  |  |  |  |  |  |  |  |  |  |

<210> SEQ ID NO 4
<211> LENGTH: 129
<212> TYPE: PRT
<213> ORGANISM: Papillomavirus Capsid Protein

<400> SEQUENCE: 4

Asn Gln Met Phe Ile Thr Val Val Asp Asn Thr Arg Asn Thr Asn Phe
1               5                   10                  15

Ser Ile Ser Val Tyr Thr Glu Gly Gly Gln Ile Lys Asp Ile Arg Asp
            20                  25                  30

Tyr Thr Ser Thr Gln Phe Arg Glu Tyr Leu Arg His Val Glu Glu Tyr
        35                  40                  45

Glu Ile Ser Val Ile Leu Gln Leu Cys Lys Ile Pro Leu Lys Ala Glu
    50                  55                  60

Val Leu Ala Gln Ile Asn Ala Met Asn Ser Ser Leu Leu Glu Asp Trp
65                  70                  75                  80

Gln Leu Gly Phe Val Pro Thr Pro Asp Asn Pro Ile His Asp Thr Tyr
                85                  90                  95

Arg Phe Ile Asp Ser Leu Ala Thr Arg Cys Pro Asp Lys Asn Pro Pro
            100                 105                 110

Lys Glu Lys Pro Asp Pro Tyr Glu Gly Leu Asn Phe Trp Asn Val Asp
        115                 120                 125

Leu

<210> SEQ ID NO 5
<211> LENGTH: 380
<212> TYPE: DNA
<213> ORGANISM: Papillomavirus Capsid Protein
<220> FEATURE:
<221> NAME/KEY: CDS
<222> LOCATION: (1)..(378)

<400> SEQUENCE: 5

|  |  |  |  |  |  |  |  |  |  |  |  |  |  |  |  |
|---|---|---|---|---|---|---|---|---|---|---|---|---|---|---|---|
| aat | cag | atg | ttt | gtt | act | gta | gca | gat | aat | aca | aga | aat | act | aat | ttt | 48 |
| Asn | Gln | Met | Phe | Val | Thr | Val | Ala | Asp | Asn | Thr | Arg | Asn | Thr | Asn | Phe |  |
| 1 |  |  |  | 5 |  |  |  |  | 10 |  |  |  |  | 15 |  |  |
| agt | att | agt | gta | tct | aca | gat | ggc | aat | ata | cca | cag | gaa | tat | gat | tct | 96 |

```
Ser Ile Ser Val Ser Thr Asp Gly Asn Ile Pro Gln Glu Tyr Asp Ser
            20                  25                  30 tca aat att aga gaa ttt tta aga cac gtg gaa gaa tat caa att tca      144
Ser Asn Ile Arg Glu Phe Leu Arg His Val Glu Glu Tyr Gln Ile Ser
            35                  40                  45 gta att ttg cag cta tgt aaa gta tca ttg gat cca gat att tta gct      192
Val Ile Leu Gln Leu Cys Lys Val Ser Leu Asp Pro Asp Ile Leu Ala
 50                  55                  60 caa atc aat gct atg aat tct gga atc tta gaa gac tgg caa tta ggg      240
Gln Ile Asn Ala Met Asn Ser Gly Ile Leu Glu Asp Trp Gln Leu Gly
 65                  70                  75                  80 ttt att cct gtc cca gat aac tca gtt cat gac aca tac aga tat att      288
Phe Ile Pro Val Pro Asp Asn Ser Val His Asp Thr Tyr Arg Tyr Ile
                 85                  90                  95 aat tca tta gct act aaa tgt cca gct aaa gta cca ccg aca gaa aga      336
Asn Ser Leu Ala Thr Lys Cys Pro Ala Lys Val Pro Pro Thr Glu Arg
            100                 105                 110 gaa gat cct ttt gct aag tat gtg ttc tgg aat gta gat cta ac           380
Glu Asp Pro Phe Ala Lys Tyr Val Phe Trp Asn Val Asp Leu
            115                 120                 125
```

<210> SEQ ID NO 6
<211> LENGTH: 126
<212> TYPE: PRT
<213> ORGANISM: Papillomavirus Capsid Protein

<400> SEQUENCE: 6

```
Asn Gln Met Phe Val Thr Val Ala Asp Asn Thr Arg Asn Thr Asn Phe
 1               5                  10                  15

Ser Ile Ser Val Ser Thr Asp Gly Asn Ile Pro Gln Glu Tyr Asp Ser
            20                  25                  30

Ser Asn Ile Arg Glu Phe Leu Arg His Val Glu Glu Tyr Gln Ile Ser
            35                  40                  45

Val Ile Leu Gln Leu Cys Lys Val Ser Leu Asp Pro Asp Ile Leu Ala
 50                  55                  60

Gln Ile Asn Ala Met Asn Ser Gly Ile Leu Glu Asp Trp Gln Leu Gly
 65                  70                  75                  80

Phe Ile Pro Val Pro Asp Asn Ser Val His Asp Thr Tyr Arg Tyr Ile
                 85                  90                  95

Asn Ser Leu Ala Thr Lys Cys Pro Ala Lys Val Pro Pro Thr Glu Arg
            100                 105                 110

Glu Asp Pro Phe Ala Lys Tyr Val Phe Trp Asn Val Asp Leu
            115                 120                 125
```

<210> SEQ ID NO 7
<211> LENGTH: 437
<212> TYPE: DNA
<213> ORGANISM: Papillomavirus Capsid Protein
<220> FEATURE:
<221> NAME/KEY: CDS
<222> LOCATION: (1)..(435)

<400> SEQUENCE: 7

```
aat caa ctg ttt att aca gtg gtg gac aac aca aga aac aca aac ttc       48
Asn Gln Leu Phe Ile Thr Val Val Asp Asn Thr Arg Asn Thr Asn Phe
 1               5                  10                  15 agt att agt gtg tat agt gaa gca ggt aaa gta aag gat att tca gat       96
Ser Ile Ser Val Tyr Ser Glu Ala Gly Lys Val Lys Asp Ile Ser Asp
            20                  25                  30 tat gat gca aac aaa ttt agg gaa tat caa aaa cat gta gaa gaa tat      144
```

```
Tyr Asp Ala Asn Lys Phe Arg Glu Tyr Gln Lys His Val Glu Glu Tyr
         35                  40                  45 gaa att tct tta ata tta caa cta tgt aag ata cct tta aaa gcc gac       192
Glu Ile Ser Leu Ile Leu Gln Leu Cys Lys Ile Pro Leu Lys Ala Asp
 50                  55                  60 gtg ttg gca caa att aat gca atg aat cca tcg tta tta gaa gag tgg       240
Val Leu Ala Gln Ile Asn Ala Met Asn Pro Ser Leu Leu Glu Glu Trp
 65                  70                  75                  80 caa ctg ggg ttt gta cct gca cca gac aat cca ttg caa agt acc tat       288
Gln Leu Gly Phe Val Pro Ala Pro Asp Asn Pro Leu Gln Ser Thr Tyr
                 85                  90                  95 agg tat atc gat agc ttg gcc aca cca tgt cct gat aaa gtg cct acc       336
Arg Tyr Ile Asp Ser Leu Ala Thr Pro Cys Pro Asp Lys Val Pro Thr
            100                 105                 110 aaa gaa aag gaa gat cca tat gct ccg ttt aca ttt tgg aac gtt gat       384
Lys Glu Lys Glu Asp Pro Tyr Ala Pro Phe Thr Phe Trp Asn Val Asp
        115                 120                 125 ttg aca gaa aga ctt tcc ttg gaa ctg gat caa tat tct ctg gga cga       432
Leu Thr Glu Arg Leu Ser Leu Glu Leu Asp Gln Tyr Ser Leu Gly Arg
    130                 135                 140 aag tt                                                                 437
Lys
145

<210> SEQ ID NO 8
<211> LENGTH: 145
<212> TYPE: PRT
<213> ORGANISM: Papillomavirus Capsid Protein

<400> SEQUENCE: 8

Asn Gln Leu Phe Ile Thr Val Val Asp Asn Thr Arg Asn Thr Asn Phe
 1               5                  10                  15

Ser Ile Ser Val Tyr Ser Glu Ala Gly Lys Val Lys Asp Ile Ser Asp
                 20                  25                  30

Tyr Asp Ala Asn Lys Phe Arg Glu Tyr Gln Lys His Val Glu Glu Tyr
             35                  40                  45

Glu Ile Ser Leu Ile Leu Gln Leu Cys Lys Ile Pro Leu Lys Ala Asp
 50                  55                  60

Val Leu Ala Gln Ile Asn Ala Met Asn Pro Ser Leu Leu Glu Glu Trp
 65                  70                  75                  80

Gln Leu Gly Phe Val Pro Ala Pro Asp Asn Pro Leu Gln Ser Thr Tyr
                 85                  90                  95

Arg Tyr Ile Asp Ser Leu Ala Thr Pro Cys Pro Asp Lys Val Pro Thr
            100                 105                 110

Lys Glu Lys Glu Asp Pro Tyr Ala Pro Phe Thr Phe Trp Asn Val Asp
        115                 120                 125

Leu Thr Glu Arg Leu Ser Leu Glu Leu Asp Gln Tyr Ser Leu Gly Arg
    130                 135                 140

Lys
145

<210> SEQ ID NO 9
<211> LENGTH: 437
<212> TYPE: DNA
<213> ORGANISM: Papillomavirus Capsid Protein
<220> FEATURE:
<221> NAME/KEY: CDS
<222> LOCATION: (1)..(435)

<400> SEQUENCE: 9
```

-continued

| | | |
|---|---|---|
| aat cag atg ttt att act gtt gta gac aac aca cgc agc aca aat ttt<br>Asn Gln Met Phe Ile Thr Val Val Asp Asn Thr Arg Ser Thr Asn Phe<br>1               5                   10                  15 | 48 | |
| agt ata tca gtt cac aca gaa aat caa gat ata tct aaa att gac agt<br>Ser Ile Ser Val His Thr Glu Asn Gln Asp Ile Ser Lys Ile Asp Ser<br>            20                  25                  30 | 96 | |
| ttt gat gca act cag ttt agg gaa tac tta aga cat gta gag gaa tat<br>Phe Asp Ala Thr Gln Phe Arg Glu Tyr Leu Arg His Val Glu Glu Tyr<br>        35                  40                  45 | 144 | |
| gag att tct ata ata tta cag tta tgt aag att cct ctg aaa gca gaa<br>Glu Ile Ser Ile Ile Leu Gln Leu Cys Lys Ile Pro Leu Lys Ala Glu<br>    50                  55                  60 | 192 | |
| gtc tta gca caa att aat gca atg aat tct tca tta ctt gaa gac tgg<br>Val Leu Ala Gln Ile Asn Ala Met Asn Ser Ser Leu Leu Glu Asp Trp<br>65                  70                  75                  80 | 240 | |
| caa ctt ggc ttt gtg ccg acg cct gat aat cca att cat gat acg tac<br>Gln Leu Gly Phe Val Pro Thr Pro Asp Asn Pro Ile His Asp Thr Tyr<br>                85                  90                  95 | 288 | |
| aga tat att gat tct ttg gca aca cgg tgc cct gat aag acg cct cca<br>Arg Tyr Ile Asp Ser Leu Ala Thr Arg Cys Pro Asp Lys Thr Pro Pro<br>            100                 105                 110 | 336 | |
| aag gaa aaa cct gat cca tat gaa aag tta cat ttt tgg aat gtg gac<br>Lys Glu Lys Pro Asp Pro Tyr Glu Lys Leu His Phe Trp Asn Val Asp<br>        115                 120                 125 | 384 | |
| ctt acc gaa cgt ctg tct tta gat tta gat caa tat cct ctg gga cga<br>Leu Thr Glu Arg Leu Ser Leu Asp Leu Asp Gln Tyr Pro Leu Gly Arg<br>    130                 135                 140 | 432 | |
| aag tt<br>Lys<br>145 | 437 | |

<210> SEQ ID NO 10
<211> LENGTH: 145
<212> TYPE: PRT
<213> ORGANISM: Papillomavirus Capsid Protein

<400> SEQUENCE: 10

Asn Gln Met Phe Ile Thr Val Val Asp Asn Thr Arg Ser Thr Asn Phe
1               5                   10                  15

Ser Ile Ser Val His Thr Glu Asn Gln Asp Ile Ser Lys Ile Asp Ser
            20                  25                  30

Phe Asp Ala Thr Gln Phe Arg Glu Tyr Leu Arg His Val Glu Glu Tyr
        35                  40                  45

Glu Ile Ser Ile Ile Leu Gln Leu Cys Lys Ile Pro Leu Lys Ala Glu
    50                  55                  60

Val Leu Ala Gln Ile Asn Ala Met Asn Ser Ser Leu Leu Glu Asp Trp
65                  70                  75                  80

Gln Leu Gly Phe Val Pro Thr Pro Asp Asn Pro Ile His Asp Thr Tyr
                85                  90                  95

Arg Tyr Ile Asp Ser Leu Ala Thr Arg Cys Pro Asp Lys Thr Pro Pro
            100                 105                 110

Lys Glu Lys Pro Asp Pro Tyr Glu Lys Leu His Phe Trp Asn Val Asp
        115                 120                 125

Leu Thr Glu Arg Leu Ser Leu Asp Leu Asp Gln Tyr Pro Leu Gly Arg
    130                 135                 140

Lys
145

```
<210> SEQ ID NO 11
<211> LENGTH: 389
<212> TYPE: DNA
<213> ORGANISM: Papillomavirus Capsid Protein
<220> FEATURE:
<221> NAME/KEY: CDS
<222> LOCATION: (1)..(387)

<400> SEQUENCE: 11 aat caa atg ttt att aca gtt gta gac aac acg cga aac acc aat ttc      48
Asn Gln Met Phe Ile Thr Val Val Asp Asn Thr Arg Asn Thr Asn Phe
1               5                  10                  15 agt ata tct ata tct agt gaa aat caa gat ata cag caa ata caa tca      96
Ser Ile Ser Ile Ser Ser Glu Asn Gln Asp Ile Gln Gln Ile Gln Ser
            20                  25                  30 tat gac tca caa aag ttt agg gaa tat tta agg cac gta gaa gaa tat     144
Tyr Asp Ser Gln Lys Phe Arg Glu Tyr Leu Arg His Val Glu Glu Tyr
        35                  40                  45 gaa att tct att att tta cag ttg tgt aag att cca cta caa gca gaa     192
Glu Ile Ser Ile Ile Leu Gln Leu Cys Lys Ile Pro Leu Gln Ala Glu
    50                  55                  60 gtt tta gca caa ata aat gca atg aac ccc tcc tta cta gag gat tgg     240
Val Leu Ala Gln Ile Asn Ala Met Asn Pro Ser Leu Leu Glu Asp Trp
65                  70                  75                  80 cag tta gga ttt gtg cca act ccc gat aat cct atc cag gac aca tac     288
Gln Leu Gly Phe Val Pro Thr Pro Asp Asn Pro Ile Gln Asp Thr Tyr
                85                  90                  95 aga ttt att gat tcc tta gct acc agg tgt ccc gat aaa aat cca cca     336
Arg Phe Ile Asp Ser Leu Ala Thr Arg Cys Pro Asp Lys Asn Pro Pro
            100                 105                 110 aag gaa aaa cct gat cct tat gaa aaa tta aca ttc tgg aat gta gat     384
Lys Glu Lys Pro Asp Pro Tyr Glu Lys Leu Thr Phe Trp Asn Val Asp
        115                 120                 125 cta ac                                                              389
Leu

<210> SEQ ID NO 12
<211> LENGTH: 129
<212> TYPE: PRT
<213> ORGANISM: Papillomavirus Capsid Protein

<400> SEQUENCE: 12

Asn Gln Met Phe Ile Thr Val Val Asp Asn Thr Arg Asn Thr Asn Phe
1               5                  10                  15

Ser Ile Ser Ile Ser Ser Glu Asn Gln Asp Ile Gln Gln Ile Gln Ser
            20                  25                  30

Tyr Asp Ser Gln Lys Phe Arg Glu Tyr Leu Arg His Val Glu Glu Tyr
        35                  40                  45

Glu Ile Ser Ile Ile Leu Gln Leu Cys Lys Ile Pro Leu Gln Ala Glu
    50                  55                  60

Val Leu Ala Gln Ile Asn Ala Met Asn Pro Ser Leu Leu Glu Asp Trp
65                  70                  75                  80

Gln Leu Gly Phe Val Pro Thr Pro Asp Asn Pro Ile Gln Asp Thr Tyr
                85                  90                  95

Arg Phe Ile Asp Ser Leu Ala Thr Arg Cys Pro Asp Lys Asn Pro Pro
            100                 105                 110

Lys Glu Lys Pro Asp Pro Tyr Glu Lys Leu Thr Phe Trp Asn Val Asp
        115                 120                 125

Leu
```

<210> SEQ ID NO 13
<211> LENGTH: 380
<212> TYPE: DNA
<213> ORGANISM: Papillomavirus Capsid Protein
<220> FEATURE:
<221> NAME/KEY: CDS
<222> LOCATION: (1)..(378)

<400> SEQUENCE: 13

```
aat caa ctg ttt gtt aca gtt gca gat aat aca agg aat acc aat ttt        48
Asn Gln Leu Phe Val Thr Val Ala Asp Asn Thr Arg Asn Thr Asn Phe
  1               5                  10                  15 act ata agt gta aca tct aat ggt acc ccc ata gca gaa tat gat tcc        96
Thr Ile Ser Val Thr Ser Asn Gly Thr Pro Ile Ala Glu Tyr Asp Ser
                 20                  25                  30 aaa act att aga gaa ttt tta agg cac gta gaa gaa tat cag ttg tcc       144
Lys Thr Ile Arg Glu Phe Leu Arg His Val Glu Glu Tyr Gln Leu Ser
             35                  40                  45 atg ata ttg caa tta tgt aaa gta cct tta aaa gca gaa gtt tta tcc       192
Met Ile Leu Gln Leu Cys Lys Val Pro Leu Lys Ala Glu Val Leu Ser
 50                  55                  60 cag att aat gct atg aat tca ggt att ttg gag gag tgg cag tta ggt       240
Gln Ile Asn Ala Met Asn Ser Gly Ile Leu Glu Glu Trp Gln Leu Gly
 65                  70                  75                  80 ttt gtg cct aca cca gac aac tct gta cat gat att tat aga tat att       288
Phe Val Pro Thr Pro Asp Asn Ser Val His Asp Ile Tyr Arg Tyr Ile
                 85                  90                  95 gac tca aaa gca aca aaa tgt ccc gat gca gtg cct gca aaa gaa aaa       336
Asp Ser Lys Ala Thr Lys Cys Pro Asp Ala Val Pro Ala Lys Glu Lys
            100                 105                 110 gaa gat cca ttt gac aaa tat aca ttt tgg aat gta gat cta ac            380
Glu Asp Pro Phe Asp Lys Tyr Thr Phe Trp Asn Val Asp Leu
            115                 120                 125
```

<210> SEQ ID NO 14
<211> LENGTH: 126
<212> TYPE: PRT
<213> ORGANISM: Papillomavirus Capsid Protein

<400> SEQUENCE: 14

```
Asn Gln Leu Phe Val Thr Val Ala Asp Asn Thr Arg Asn Thr Asn Phe
  1               5                  10                  15

Thr Ile Ser Val Thr Ser Asn Gly Thr Pro Ile Ala Glu Tyr Asp Ser
                 20                  25                  30

Lys Thr Ile Arg Glu Phe Leu Arg His Val Glu Glu Tyr Gln Leu Ser
             35                  40                  45

Met Ile Leu Gln Leu Cys Lys Val Pro Leu Lys Ala Glu Val Leu Ser
 50                  55                  60

Gln Ile Asn Ala Met Asn Ser Gly Ile Leu Glu Glu Trp Gln Leu Gly
 65                  70                  75                  80

Phe Val Pro Thr Pro Asp Asn Ser Val His Asp Ile Tyr Arg Tyr Ile
                 85                  90                  95

Asp Ser Lys Ala Thr Lys Cys Pro Asp Ala Val Pro Ala Lys Glu Lys
            100                 105                 110

Glu Asp Pro Phe Asp Lys Tyr Thr Phe Trp Asn Val Asp Leu
            115                 120                 125
```